United States Patent
De Nora et al.

(10) Patent No.: US 6,503,724 B1
(45) Date of Patent: Jan. 7, 2003

(54) FIBRINOPEPTIDES IN SALIVA AS INDICATOR OF BLOOD COAGULATION STATUS

(75) Inventors: Matteo De Nora, Monaco (MC); Jacob R. Blasius, Boca Raton, FL (US)

(73) Assignee: Link Enterprises Corporation, Panama (PA)

( * ) Notice: Subject to any disclaimer, the term of this patent is extended or adjusted under 35 U.S.C. 154(b) by 0 days.

(21) Appl. No.: 09/673,085

(22) PCT Filed: May 14, 1999

(86) PCT No.: PCT/IB99/00869

§ 371 (c)(1),
(2), (4) Date: Oct. 11, 2000

(87) PCT Pub. No.: WO99/60409

PCT Pub. Date: Nov. 25, 1999

(30) Foreign Application Priority Data

May 18, 1998 (EP) .............................. 98820460

(51) Int. Cl.⁷ ........................... C12Q 1/56; G01N 31/00
(52) U.S. Cl. .............................. 435/13; 436/16; 436/18
(58) Field of Search .............................. 435/13; 436/16, 436/18

(56) References Cited

U.S. PATENT DOCUMENTS

| 3,960,669 A | 6/1976 | Innerfield | ................. | 195/103.5 |
| 5,071,954 A | 12/1991 | Pelzer et al. | ................. | 530/324 |

FOREIGN PATENT DOCUMENTS

WO 9960409 A1 * 5/1999

OTHER PUBLICATIONS

Thrombosis Research, vol. 67, No. 4, pp. 429–434, Aug. 15, 1992. Cited in the PCT search rpt.
American Journal of Hematology, vol.57, No. 3, pp. 193–199, Mar. 1998. Cited in the PCT search rpt.
Thrombosis Research, vol. 13, No. 3, pp. 551–556, Sep. 1978. Cited in the PCT search rpt.
Annal New York Academy of Science, vol. 370, pp. 398–413, 1981. Cited in the PCT search rpt.
British Journal of Urology, vol. 75, No. 6, pp. 712–719, Jun. 1995. Cited in the PCT search rpt.
Abstract—Derwent Publication No. 98–581163, Apr. 27, 1998. Cited in the PCT search rpt.

* cited by examiner

Primary Examiner—Louise N. Leary
(74) Attorney, Agent, or Firm—Armstrong, Westerman & Hattori, LLP

(57) ABSTRACT

A non invasive method for determining the blood coagulation status of a human or an animal is described. F1+2, F1, F2, FpA, D-dimers, F1+2 combined with F1, or F1+2 combined with F2 are measured in saliva, sputum and related biological samples. The respective concentrations are inversely correlated to the time it takes blood to coagulate and the probability of bleeding, and directly correlated to the probability of in-vivo formation of a thrombus or emboli. The method can be used in any coagulation disorder study, including congenital, acquired or drug-induced.

16 Claims, 5 Drawing Sheets

FIG.2

PROTHROMBIN TO THROMBIN CONVERSION PATHWAY

F1+2 = PROTHROMBIN FRAGMENT 1+2
F1 = PROTHROMBIN FRAGMENT 1
F2 = PROTHROMBIN FRAGMENT 2
Xa = ACTIVATED BLOOD FACTOR X
$I_1$ = INTERMEDIATE 1
$I_2$ = INTERMEDIATE 2
Va = ACTIVATED BLOOD FACTOR V
$C^{++}$ = CALCIUM
$T_H$ = HEAVY CHAIN OF THROMBIN
$T_L$ = LIGHT CHAIN OF THROMBIN
S-S = DISULFIDE BOND
NUMBERS ARE MOLECULAR WEIGHT IN DALTONS

FIG.3

GENERATION OF FIBRINOPEPTIDE A, FpA, BY THROMBIN

FIG.5
ENZYMOIMMUNOASSAY WITH LABELED ANTIBODY

FIBRINOPEPTIDES IN SALIVA AS INDICATOR OF BLOOD COAGULATION STATUS

BACKGROUND OF THE INVENTION

Blood coagulation is a complex system involving a large number of proteins that function in concert to yield hemostasis. The coagulation system is regulated by a series of proteins present in plasma and on the surface of cells. Under physiological conditions, pro- and anti-coagulant mechanisms are delicately balanced to provide hemostasis and coagulation. Disturbances in this balance result in either bleeding or thromboembolic disorders, and can be induced by medical conditions, congenital or acquired, the intake of drugs or vitamins. The most widely used tests to measure the coagulation status of a person are known as clotting assays. Clotting assays measure the clotting times of recalcified platelet-poor plasma. The prothrombin time (PT) test is performed by adding calcium and thromboplastin to citrated plasma. The term thromboplastin refers to a phospholipid-protein extract of tissues, usually lung, brain, or placenta, that contains both tissue factor and the phospholipid necessary to promote the activation of factor X by Factor VII. The standard thromboplastin is "The World Health Organization" (WHO) thromboplastin which is derived from human brain thromboplastin. PT test instruments are based upon measuring how the plasma viscosity changes over time after calcium and thromboplastin have been added to plasma. When plasma coagulates it turns from a solution to a gel which is more viscous. In the APTT test, decalcified plasma is incubated for a specified time with activating agents such as ellagic acid, silica, soy extract, or kaolin. Following incubation with the activating substance, calcium chloride is added to the plasma mixture for a clot to form. In the PTT test, plasma is incubated for 3 minutes with a reagent supplying procoagulant phospholipid and surface-active powder (e.g. micronized silica). Calcium is then added and the clotting time noted.

Although widely used, clotting assays present several drawbacks. First, clotting assays are by definition invasive, as they require some blood to be drawn from the patient. Second, they require that actual coagulation of the blood be performed in a vial, which involves delicate handling, accurate timing, and citration of plasma. Third, clotting assays depend on an additional product, thromboplastin, whose performance can be different from the reference WHO thromboplastin, requiring complicated International Normalization Ratio (INR) calculations to ensure accuracy. Finally, clotting tests are indirect tests, reflecting only indirectly fibrinopeptides and fibrinogen degradation products and other proteins related to the state of anticoagulation.

Direct measurement of prothrombin fragments in blood or serum for determining the coagulation status is known in the art (U.S. Pat. No. 5,071,954). However, these methods are invariably invasive since they require some blood to be drawn.

Measurements of at least some of the above fragments in urine may be found in various papers, for instance in A. Bezeaud and al, Thrombosis Research, 13, 3, p. 551–556 (September 1978); J. V. Sorensen and al, Thrombosis Research, 67, 4, p. 429–434 (August 1992); D. M. Weinstock and al., American J. Hematology, 57,3, p. 193–199 (March 1998).

SUMMARY OF THE INVENTION

The purpose of this invention is to use a non invasive diagnostic test technique to measure the level of blood anticoagulation induced by pharmaceuticals which prevent or reduce coagulation of blood as well as to measure and/or identify any natural or disease-induced blood disorders which effect the coagulation of blood. In addition, the invention can be used to measure the level of hypercoagulation induced by drugs, proteins and vitamins which augment coagulation of blood (procoagulant drugs). The invention is a non invasive test since it measures key substances present in saliva, filtered saliva, sputum, or the like, which are obtainable non invasively (hereunder referred to as "saliva"). The invention is usable in humans as well as in animals.

It must be pointed out at this stage that saliva and urine are very different in terms or biological roles and compositions, as well as in their enzymatic environments.

Examples of clinical applications in which the test could be used include all blood coagulation disorders, be they congenital, acquired, or drug-induced. One can mention congenital deficiencies of the intrinsic pathway of the coagulation system (hemophilia A and B, deficiencies of Fitzgerald factor and Fletcher factor), deficiencies in protein C and protein S, heparin and heparin-like therapy, Warfarin (Coumadin)-like therapy, acute thrombotic situations such as acute myocardial infarction or pulmonary embolism, Vitamin K deficiency or excess, hypofibrinogenemia, liver disease, disseminated intravascular coagulopathy, among others.

The invention produces a quantitative measurement of prothrombin fragment 1+2 (F1+2), prothrombin fragment 1 (F1), prothrombin fragment 2 (F2), fibrinopeptide A (FpA) and D-Dimers in saliva which is correlated with the coagulation time as expressed for example by prothrombin time (PT), INR, partial thromboplastin time (PTT) and activated partial thromboplastin time (APTT). Fragments F1+2, F1, F2, FpA and D-Dimers are preferably measured by means of immunoassay techniques, which measure a substance using the reaction of an antibody (immunoreagent) with an antigen (i.e. the protein to be measured). The quantification of the substance measured is determined by measuring how much of the antigen is bound to the antibody and how much of the antigen is not bound to the antibody. Enzyme-labeled, fluorescent-labeled, phosphorescent-labeled, radio-labeled, chemiluminescent-labeled and bioluminescent-labeled immunoassay techniques are for example usable to measure the concentrations of Fragments F1+2, F1, F2, FpA and D-Dimers. Capillary action, precipitation, turbidometric, diffusion, agglutination and electrophorefic immunoassay techniques can also be used in practicing the invention, as well as potentiometric, amperometric, piezoelectric and evanescent-wave immunosensors. In addition, any combination of the aforesaid assay techniques can also be employed to measure the concentrations of Fragments F1+2, F1, F2, FpA and D-Dimers in saliva.

Figure 1:
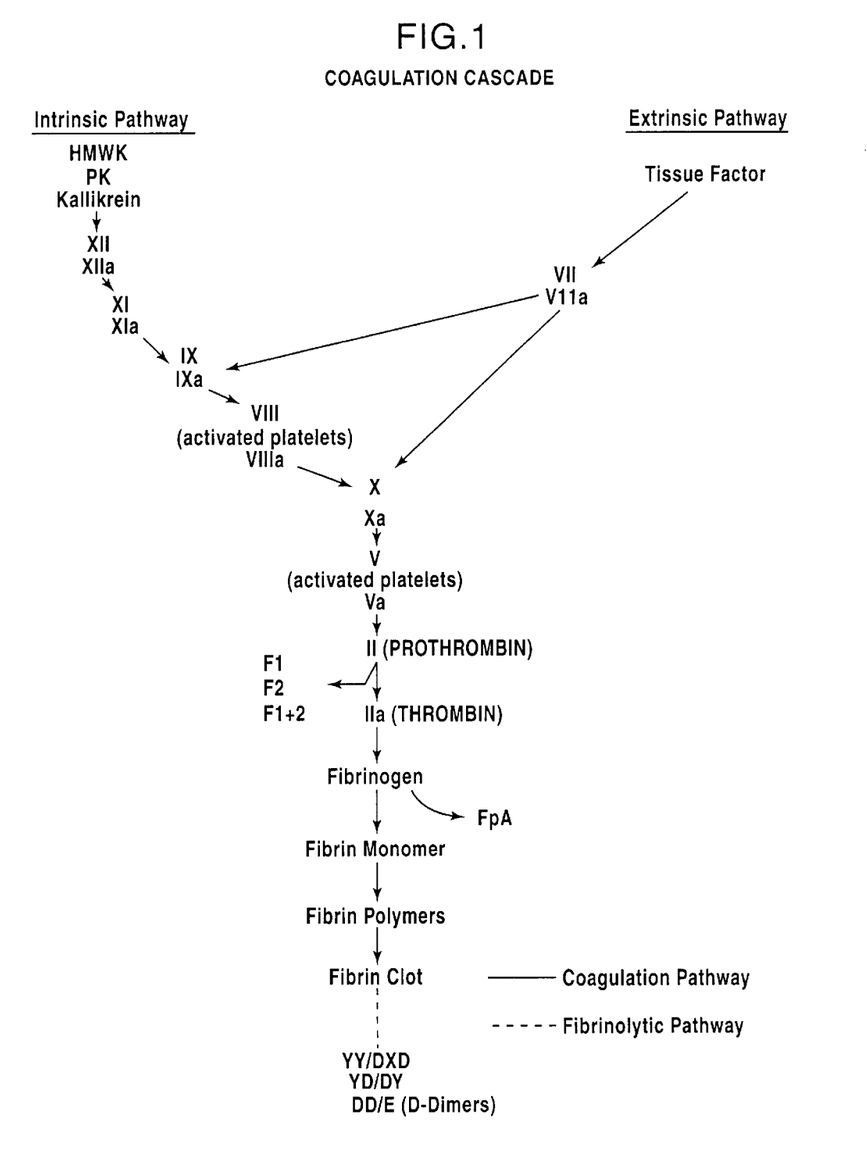
FIG. 1 is a diagram showing the coagulation cascade.

A preferred application of this invention is to control the level of any pharmaceutical which results in anticoagulation of the blood by affecting the conversion of blood Factor X to Factor Xa, which is commonly termed activated Factor X. Factor X and Factor Xa, which are in the latter stages of the coagulation cascade best correlate with the anticoagulation effect (see FIG. 1 for diagram of coagulation cascade).

Factor X is a glycoprotein of molecular weight 55,000 and composed of two polypeptide chains linked by one disulfide bond. The light and heavy chains have molecular weights of 16,000 and 38,000 daltons respectively. During the coagulation process Factor X is converted to Factor Xa by either factors IXa, and VIII or Factor VII and tissue Factor. Factor X can also be activated by other proteases such as trypsin. The activation of Factor X by each of these systems involves the cleavage of a single specific arginyl-isoleucine peptide bond in the heavy chain of Factor X. This gives rise to the formation of a glycoprotein of molecular weight 44,000 and a peptide with a molecular weight of 11,000.

A common feature of Fragments F1+2, F1, F2, FpA and D-Dimers as measured in the invention is that their concentration rises when the conversion of Factor X to Factor Xa increases, and decreases when the conversion of Factor X to Factor Xa is inhibited. The respective roles of Fragments F1+2, F1, F2, FpA and D-Dimers in coagulation is explained in the following paragraphs.

Activated blood factor X forms a -complex with activated blood factor V, phospholipid and calcium. The first step in the activation by the complex is the proteolytic cleavage of a fragment from the NH2-terminal end of prothrombin. This gives rise to what is termed intermediate II (an intermediate precursor of thrombin) and the clipped fragment referred to as prothrombin fragment 1+2. Intermediate II (which is a single chain polypeptide) is then cleaved a second time by activated factor X complex to yield a two chain (light and heavy chains) thrombin molecule.

Figure 2:
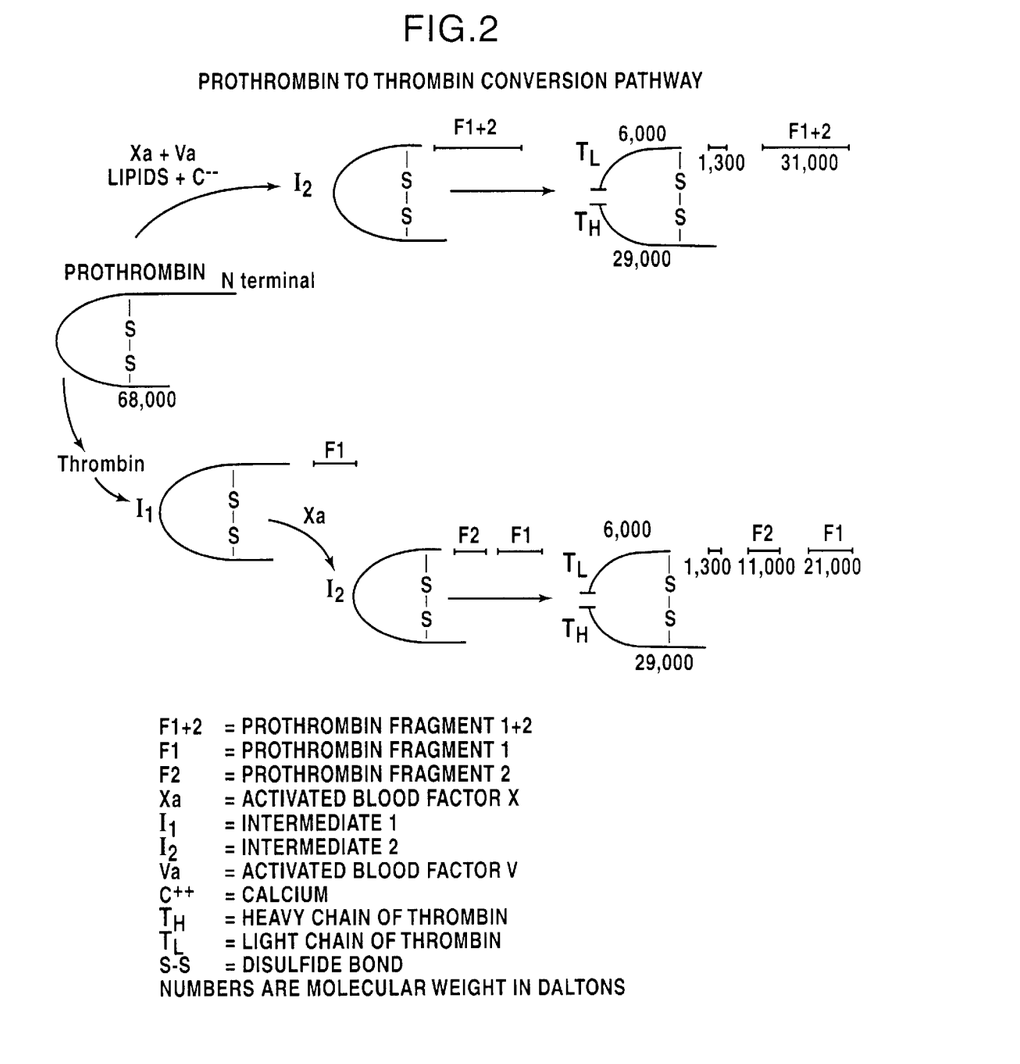
FIG. 2 is a diagram showing the Prothrombin to Thrombin conversion pathway.

Thrombin can use prothrombin as a substrate. When thrombin uses prothrombin as a substrate the cleavage pattern differs from that obtained by the activated factor X complex. Thrombin cleaves prothrombin releasing a fragment smaller than that cleaved by the activated factor X complex. This gives rise to what is termed prothrombin fragment 1 and intermediate I. This cleavage occurs without the involvement of activated factor V, phospholipid or calcium. Thrombin cannot activate prothrombin to thrombin. Activated factor X is required for the conversion to thrombin; however, activated factor X then cleaves off the remaining portion of prothrombin fragment 1+2 from intermediate I to give rise to fragment 2 and intermediate II. Intermediate II is then cleaved by activated factor X to give the thrombin molecule. Thrombin generated by the activated factor X mechanism will also cleave the prothrombin fragment 1+2 produced by the initial activated factor X cleavage to give rise to prothrombin fragment 1 and prothrombin fragment 2. See FIG. 2 for diagram of Prothrombin to Thrombin conversion pathway.

Figure 3:
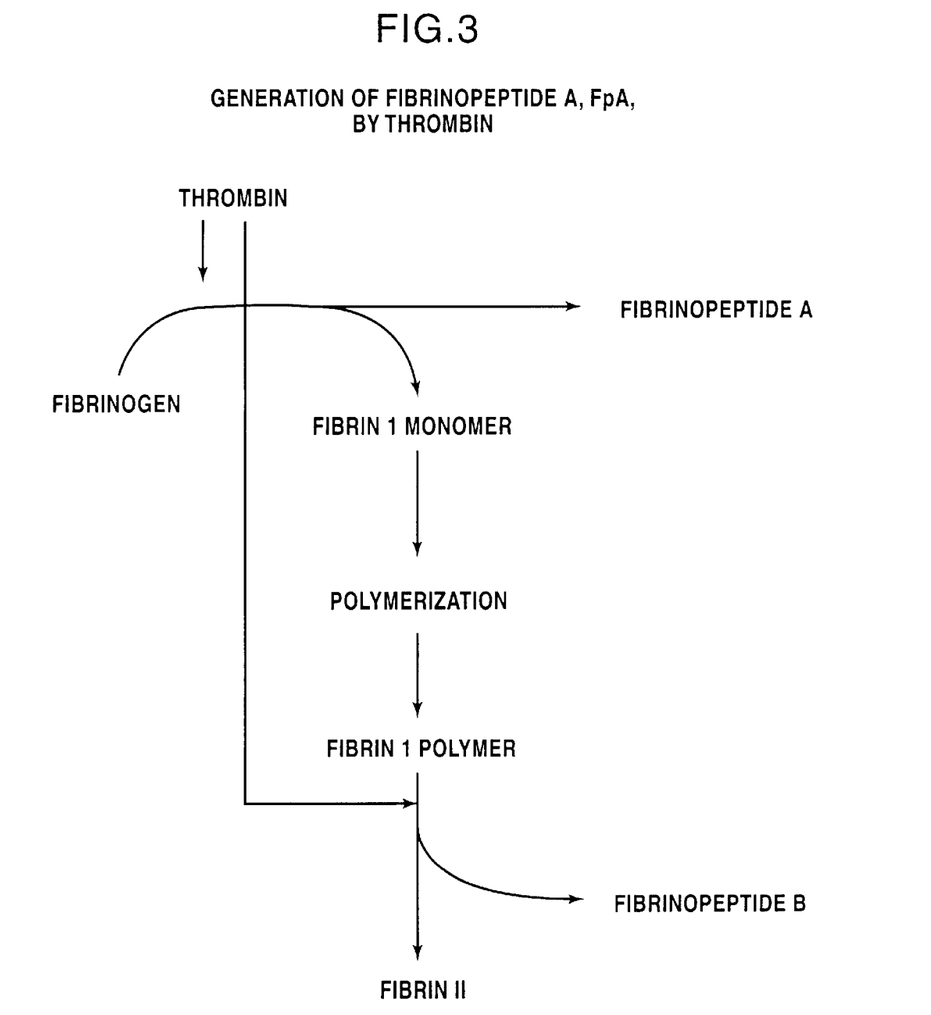
FIG. 3 is a diagram showing the generation of FpA by Thrombin.

The conversion of fibrinogen to fibrin by thrombin initially results in the formation of fibrin 1 monomer and the release of Fibrinopeptide A (FpA). Fibrin 1 monomer is able to polymerize, and thrombin can then cleave the polymer, thereby resulting in the generation of fibrin II and the release of fibrinopeptide B. When Factor Xa is inhibited by a pharmaceutical, the level of FpA will decrease. FIG. 3 shows the generation of FpA by Thrombin.

Figure 4:
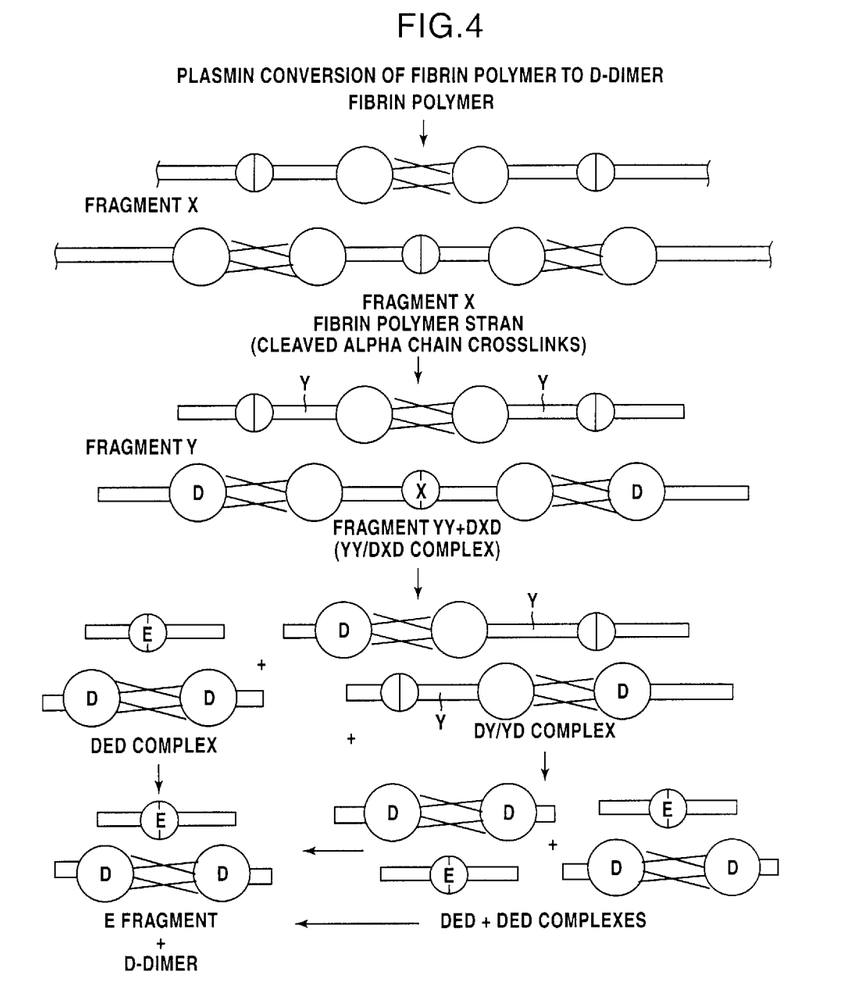
FIG. 4 is a diagram showing the generation of D-Dimers during degradation of Fibrin polymers by plasmin.

Fibrin clot Formation is initiated when thrombin cleaves fibrinopeptides A and B from the E domain of fibrinogen. The resulting soluble fibrin monomers align in a staggered end-to-end arrangement to produce protofibrils. Protofibrils later polymerize side-by-side into large, soluble fibrin oligomers. In the process of fibrinogen or fibrin degradation by plasmin within a clot, specific molecular fragments are produced called fibrinogen degradation products (FDP). Plasmin cannot distinguish between fibrinogen and fibrin : therefore, it degrades both. This results in the appearance of essentially the same fragments from fibrinogen and fibrin. FIG. 4 shows the sequence of the reactions in the degradation of fibrinogen and fibrin by plasmin and the principal products, fragment X,Y,D (D-D dimer), and E. Fragments X and Y are referred to as the early degradation products. Fragments D and E are the late degradation products. Fragment X is the first and largest fragment formed (250,000 Daltons). Fragment X is the result of plasmin cleavage of the terminal portion of the alpha chains from a fibrin polymer, leaving isolated fibrin stands. Fragment X is then cleaved by plasmin to form two fragments called Y (YY) and an intermediate complex DXD. This complex is further cleaved into intermediate complexes DED and DYND until finally fragments E and D (D-D dimer) are formed.

The molecular weight of each fragment is as shown below:

| | | |
|---|---|---|
| FRAGMENT X | = | 250,000 DALTONS |
| FRAGMENT Y | = | 150,000 DALTONS |
| FRAGMENT E | = | 50,000 DALTONS |
| D-D DIMER | = | 180,000 DALTONS |

In summary, any pharmaceutical which reduces the conversion of Factor X to Factor Xa will reduce the level of Fragment 1+2, F1, F2, FpA and D-Dimer in body fluids. Reductions in Factor Xa result in blood taking a longer time to coagulate. Therefore, the quantity of Fragment 1+2, F1, F2, FpA and D-Dimer is inversely proportional to the level of anticoagulation. The less Fragment 1+2, F1, F2, FpA and D-Dimer in saliva, the longer it will take for blood to coagulate. Conversely, the more Fragment 1+2, F1, F2, FpA and D-Dimer in saliva, the less time it will take the blood to coagulate.

Both saliva and urine are excreted by the body and both substances are know to contain blood proteins. The advantages and disadvantages of using these medium to diagnose the state of coagulation indicates that saliva would be the preferred medium if the concentration of the coagulation markers in saliva are directly proportional to their concentration in blood.

Compared to urine, saliva presents a number of crucial advantages, for instance:

nearly everyone can salivate at any time of day and for multiple times, privacy is not required to provide a specimen in contrast to urine specimens, the extensive vascular bed in the salivary glands offers a good pathway of blood components to the inside of the mouth, individuals find handling their saliva is more tasteful than handling their urine equally applicable to men and women, women have blood in their urine during menstruation, collection of specimens can be fast, so there is less time for deleterious substances in the saliva to effect the concentration of the coagulation marker, less individuals have salivary gland problems than have kidney problems.

By contrast, disadvantages of saliva over urine are of low importance:

gingival crevicular fluid may contain blood, saliva flow rate varies due to many factors (for example stress and degree of hydration).

Moreover, the transport of coagulation markers to saliva is a more direct route from blood than urine. The urine is stored in the bladder before excretion and this is a major drawback of urine use as a diagnotic medium.

The invention is relating as well to a non invasive device for doing in-vitro analysis of the concentration of the coagulation markers which best correlate to the state of anticoagulation of individuals undergoing Warfarin therapy so that the individuals can control their Warfarin dosage, thereby reducing visits to care-giver offices and increasing the accuracy of dosing. The functional requirements of the test are: be non invasive; not require a blood sample to be withdrawn from a user; be able to be used at home by persons undergoing Warfarin therapy; be able to be carried out by persons of average intelligence and motor skills after receiving minimal training; results to be readable by the users eye or an inexpensive device such as a photometer, densitometer or calorimeter; be cost effective in that the cost of the test is to be less than the cost charged by physicians and clinics for the patient visit and the cost of the test procedure; be capable of accurately measuring for a person which is stabilized on Warfarin therapy, the coagulation markers over the expected range in the saliva being analyzed; not require meticulous attention to specimen acquisition and processing; only require "spot" saliva; portable due to small size and weight; provides rapid results, preferably less than 15 minutes; provides a quantitative result, preferably in the form of a permanent record.

Such an at home test saves time and money, helps those patients which have a hardship traveling to institutions, the debilitated and those lacking adequate transportation.

An at home test also improves anticoagulation therapy and safety as self monitoring has proven more accurate than institution based monitoring, especially for patients interested in their well being. It induces patients to have a greater responsibility for managing one's own therapy, allows for more frequent monitoring, especially when fluctuating PT values require adjusting of the anticoagulant dose.

Studies conducted of individuals which self monitor and control Warfarin dosage compared to those which are monitored and controlled by a clinic show that the self controlled have less complications and better control. Subjects also would rather self control than spend their time going to a clinic.

DETAILED DESCRIPTION

Figure 5:
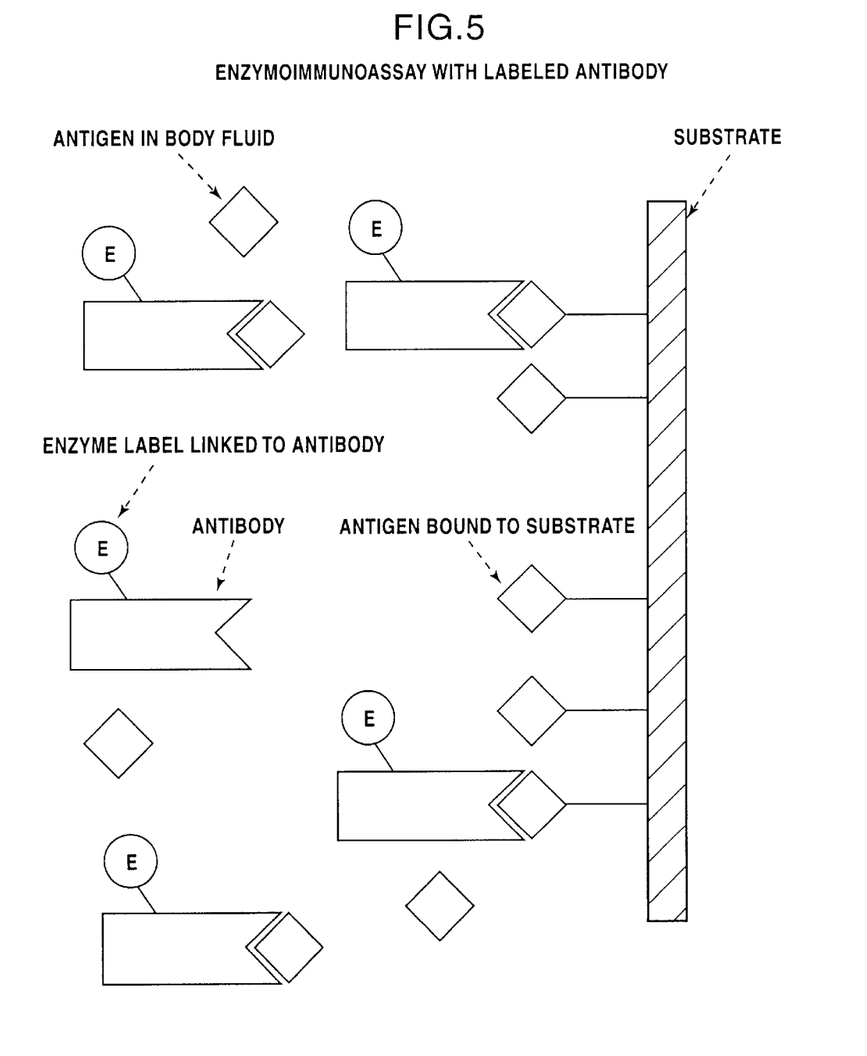
FIG. 5 is a diagram showing the principle of an enzymoimmunoassay as used in practicing the invention.

In a preferred embodiment of the invention, fragments F1+2, F1, F2, FpA, and D-dimers are measured by immunoassay technology, preferably enzymoimmunoassay technology, in which a labeled antibody is used to determine the amount of protein (antigen) in body fluids. In an enzymoimmunoassay, a known amount of antigen (here fragment F1+2, F1, F2, FpA, D-dimers) is bound to the substrate (for example the glass wall of a test tube) of the test. The body fluid to be tested containing the antigen to be measured (F1+2, F1, F2, FpA, D-dimers) is then put in contact with the substrate. This method depends on the distribution of a limited amount of enzyme-labeled antibody, which is added to the body fluid, between the antigen on the substrate and the antigen in body fluid. Maximum binding of the labeled antibody to the immobilized antigen will take place in the absence of antigen to be measured. As the concentration of antigen to be measured in the body fluid increases, the amount of labeled antibody which will attach to the antigen bound to the substrate will proportionally decrease. This result is due to a portion of the labeled antibody attaching to the immobilized antigen as well as the antigen in body fluid (see FIG. 5). Measurement of the amount of antibody attached to the antigen which is bound to the substrate allows for the calculation of the amount of antigen which is in the body fluid.

The combination of antigen and antibody are given below.

| ANTIGEN IN SOLUTION | ANTIGEN COATED ON SUBSTRATE | ANTIBODY |
|---|---|---|
| Fragment 1 + 2 | Fragment 1 + 2 | Enzygnost F1 + 2 produced by Behringwerke AG- Marburg, Germany or any other commercially available Fragment 1 + 2 antibody |
| F1 | F1 | BI 9-1 developed by Flinders Medical Center, Adelaide, Australia or any other commercially available F1 antibody |
| F2 | F2 | Any commercially available F2 antibody |
| FpA | FpA | One of the commercially available FpA antibodies produced by Boehringer Mannheim or any other manufacturer of FpA antibody |
| D-Dimer | D-Dimer | DD-36B monoclonal antibody produced by Dade, Miami, Florida or any other manufactures of D- Dimer antibody |

This ELISA employs an antigen attached to the substrate. The following examples will show, that an ELISA in which an antibody is attached to the substrate may be employed as well.

EXAMPLES

A preferred embodiment of the invention is to measure F1+2, F1, F2, FpA, D-dimers, F1+2 combined with F1, or F1+2 combined with F2 in saliva.

A group of 13 individuals undergoing Warfarin anticoagulation therapy (®Coumadin which is manufactured by DuPont Merck Pharmaceuticals) for the medical conditions of atrial fibrillation and mechanical heart values were tested for the concentration of the coagulation markers in their plasma and saliva.

It should be noted here that Warfarin is given just as an example for an anticoagulant therapy; the scope of the invention extends to all similar anticoagulant therapies and of course any procoagulant therapy.

All subjects in this study were recruited from patients who were undergoing Warfarin therapy for more than two weeks and whose state of anticoagulation was relatively stable so that dosing levels were not fluctuating.

All subjects in this study received the standard anticoagulation therapy for the state of anticoagulation required for the subject's particular disease or physical condition as determined by the subject's physician.

The study included 12 subjects which met all inclusion criteria. A thirteenth subject was included who was stabilized on Warfarin but later stopped taking Warfarin due to no longer requiring therapy. They consisted of a mix of 7 males between the ages of 46 to 67 years old and 6 females between the ages of 59 to 74 years old. They were stratified into the following three classes:

Class# 1—Subjects with a prosthetic mechanical heart valve receiving long term Warfarin therapy and being controlled to an anticoagulation level of 2.5–3.5 INR. These subjects were patients which were normally having their prothrombin time checked every 1 to 3 weeks.

Class# 2—Subjects with atrial fibrillation receiving long term Warfarin therapy and being controlled to an anticoagulation level of 2.0–3.0 INR. These subjects were patients which were normally having their prothrombin time checked every 1 to 3 weeks.

Class# 3—Subjects with atrial fibrillation receiving Warfarin therapy and being controlled to an anticoagulation level of 2.0–3.0 INR. These subjects were patients which have been stabilized on Warfarin therapy for one month or more, but were expected to end their therapy in 3 to 4 months. These subjects were patients which were normally having their prothrombin time checked every 1 to 3 weeks. Alternately, these subjects could be individuals which were beginning Warfarin therapy. If they were beginning Warfarin therapy, they were included in the study if they had not been undergoing anticoagulation therapy or thrombolytic therapy in the previous 5 days.

Additionally, the subjects were required to provide specimens prior to the beginning of Warfarin treatment or 7 days after Warfarin treatment was ceased.

The purpose of Class# 1 and # 2 was to measure the concentration of coagulation markers for subjects which are stabilized on long term Warfarin therapy. The purpose of Class# 3 was to measure how the concentration of the coagulation markers change as the subjects which were stabilized are then taken off Warfarin therapy or conversely how the concentration of the coagulation markers change as the subjects are initiated and then stabilized on Warfarin therapy.

Of the 13 subjects which completed the study, 7 were in Class# 1, 5 were in Class# 2, and 1 was in Class# 3.

The subjects followed the a specific diet and living habit regiment during the study period, with no medications and illicit drug use, with particular attention to drugs potentiating Warfarin's anticoagulation effect and drugs inhibiting Warfarin's anticoagulation effect. They were tested for illicit drug use using the SmithKline Drug Abuse Panel 10–50.

The subjects provided blood, urine and saliva specimens sequentially on the same day usually in the morning, always within plus or minus 1 hour of a regularly scheduled time (e.g. if on the subject's first day of providing a specimen the specimen collection was at 11:00 AM then every succeeding time a specimen was provided it was between 10:00 AM and 12:00 noon). This time constraint was imposed to minimize the effects of the circadian rhythm of a person's coagulation system. Of the 89 sets of specimens collected only 7 were not collected according to the time constraint.

No specimens were collected from subjects with blood in their urine or bleeding gums. The urine specimen was the first specimen collected so as to determine if there was blood in the urine.

Urine Specimen Collection:

Each time the subjects provided specimens they provided 5 ounces (approximately 140 g) of spot urine which was immediately frozen at −20 degrees centigrade.

Blood Specimen Collection:

Two 4.5 ml venous blood specimens were collected each time the subjects provided blood specimens. One blood specimen was used for the determination of prothrombin time within 24 hrs. The other blood specimen was for determination of coagulation marker concentrations. Normal venous blood collection procedures were used. Each blood specimen was collected during the same visit and within moments before or after the saliva or urine specimens were collected. Each blood specimen was collected with a Becton Dickinson Coagulation Vacutainer tube with siliconized interior (catalog# 366415) containing 0.5 ml 0.105 M buffered sodium citrate anticoagulant.

The blood was collected per NCCLS H3-A2 procedures so as to have 9 Vol venous blood and 1 Vol sodium citrate. Care was taken to not force blood from the subjects' veins. Within 1 hour of sample collection the whole blood was centrifuged for 10 minutes at 3000 rpm. The supernatant plasma was withdrawn and immediately stored at −20 degrees centigrade.

Saliva Specimens Collection:

The subjects were first asked if his gums have been bleeding or if his gums bled the last time subject brushed his teeth so as to avoid collecting saliva which may have contained blood or saliva which may have excessive amounts of fluid from the gingival crevice. No saliva samples were collected from subjects with bleeding gums. Two saliva samples were simultaneously collected. Approximately 2 ml of saliva was collected from each subject. The saliva collection device is the Saliva Sampler manufactured by Saliva Diagnostic Systems. The device consists of a collection tube, a cotton collector pad with a built in indicator and a filter (Porex Blood Serum Filter) which separates out cellular matter from the whole saliva. The saliva collection tube as supplied by the manufacturer contains a preservative transport buffer. This solution was removed and the collection tubes were washed and sterilized before being used.

The collector pad collects between 0.8 to 1.3 ml of whole saliva in 3 minutes (normal range 1–7 minutes). The collector pad assembly has a built in indicator which turns color from white to blue when the collector pad is saturated.

The saliva which was collected is the saliva from the sublingual gland and submaxillary gland located under the tongue at the floor of the mouth. Contact with the gingival crevice (area between the gums and the tooth) was avoided. The collection technique was unstimulated saliva collection. That is the saliva being collected was with the subject not chewing or otherwise stimulating the inside of the mouth.

The sequential steps of saliva were as follows:

1.) Subject thoroughly rinsed mouth with deionized water and then swallow three times to void mouth of saliva and rinse water;

2.) Subject was instructed that during saliva collection he was to minimize orofacial movements and not suck or chew the saliva collection pad or swallow the saliva;

3.) Subject sat erect, with head tilted slightly forward (No more than a 15 degrees downward angle);

4.) Subject waited for 5 minutes for saliva to collect in mouth;

5.) One collection pad was placed on the right side of the mouth under the tongue in the floor of the mouth to the right of the tongue. The second collection pad was placed on the left side of the mouth under the tongue in the floor of the mouth to the left of the tongue;

6.) The subject closed his mouth and kept the collection pads in his mouth for a minimum of 3 minutes. The pads were removed when the indicator turned from white to blue; if after 15 minutes the indicator did not turn blue the collection pad was discarded and the procedure was restarted at step 4;

7.) Each collection pad was placed into its collection tube and the tube was capped; the collection tube was then flicked to detach the collection pad from its stem;

8.) The Porex filter was inserted into the collection tube and the filtered saliva was then poured into a cryotube. The cryotube was immediately frozen at −20° C.

The amount of filtered saliva recovered by the above procedure was between 0.250 ml and 0.50 ml per collection pad.

INR Measurement:

The blood samples collected from the clinical trial subjects were immediately frozen at −20° C. Within 24 hours of blood sample collection, the samples prothrombin time and INR were measured in the laboratory. All INR results were obtained by using the same lot of thromboplastin on the same PT test equipment. The test equipment and thromboplastin are manufactured by Organon Teknika. The thromboplastin had an ISI=1.29. The control group PT reference range is 12.1 to 14.5 seconds with 12.8 seconds used for all PT calculations.

The important points are that the patients were stabilized on Warfarin and they were free of diseases and drugs which would interfere with the therapy and cause blood to be in the urine or saliva.

The testing of the saliva to determine the concentration of the coagulation markers was conducted with ELISA. The ELISA test only requires 0.100 milliliters of filtered saliva. It is best to collect 0.250 milliliters of filtered saliva so that the test can be run in duplicate which is standard procedure with ELISA tests.

The determination of the concentration of F1, F1+2, D-Dimer and FpA in saliva used ELISA similar to the following which describes the construction and use of an ELISA to determine the concentration of F1 in saliva specimens. However, ELISA is not the only type of immunoassay which will work in this application.

DEVELOPMENT OF F1 IMMUNOASSAY AND ELISA TEST PROCEDURE

Development of F1 Antibody:

An F1 antibody to human prothrombin fragment 1, F1, antigen was developed by injecting human prothrombin fragment 1 into a New Zealand White rabbit. The rabbit then produces an F1 antibody which is a polyclonal antibody.

New Zealand White rabbits were injected intradermally with 1 ml human prothrombin fragment 1 antigen emulsified with Freund's complete adjuvant on day 1. On days 6 and 13 the rabbits were intradermally injected with Freund's incomplete adjuvant. Intra-muscular booster injections were repeated once per month thereafter. The rabbit serum was harvested 6 weeks after the initial injection and stored at −20° C.

Purification of F1 Antibody:

The first step is to grossly purify the rabbit serum containing the F1 antibody by the protein A purification method, (Boliag, D. M., et. al., 1966, Protein Methods, 2nd Ed. 415 pages, Wiley-Liss, NY, N.Y.). An affinity column containing Affi-Gel Protein A Agarose is prepared. The rabbit serum is processed through the column which binds the F1 antibody and the other antibodies in the serum. The F1 antibody and other antibodies are recovered from the column with an elution buffer.

The second step is to dialyze the solution obtained in step 1 against 3×2 liters of PBS. The dialyzed solution is then passed through a F1 affinity column (the affinity column contains F1 antigen) 10 times to capture the F1 antibody contained in the solution. The F1 affinity column is washed with PBS to remove the unbound and nonspecifically bound antibodies. Actisep elution medium (Sterogene Bioseparations, cat.# 9701–01) is added to the column and incubated for 10 minutes at room temperature. The eluate which contains the F1 antibody is collected for additional processing.

The third step is to remove the antibodies which will cross react with F2 antigen. The solution obtained in step 2 is passed through an affinity column containing F2 antigen. Ten passes are performed to remove the antibodies which cross react with F2. The final solution is a purified F1 polyclonal antibody which has no significant cross reactivity with F2 antigen.

CONSTRUCTION OF SALIVA F1 ELISA

The following describes the construction of a sandwich enzyme labeled immunoassay, ELISA. The ELISA uses the purified F1 antibody bound to a solid substrate as the capture antibody to remove F1 antigen from saliva specimens. The detection antibody is F1 antibody labeled with Horseradish Peroxidase, HRP.

Plate Coating:

Mix F1 antibody and PBS to achieve the desired concentration of F1 antibody on the surface of the ELISA plate. Pipette 100 μl of coating solution into the wells of a CoStar EIA/RIA 8-Well strip plate. Place plates in a humid container and store overnight at room temperature.

Plate Blocking and Drying:

Aspirate coating solution from each plate well and wash two times. Immediately fill each plate well with blocking buffer. Place plates in a humidified container and store overnight at room temperature. The following morning remove the blocking solution and dry the plates in a vacuum drier.

Labeling of F1 Antibody with HRP:

F1 antibody is labeled with HRP to produce the detection antibody which attaches to the F1 antigen which is captured from the saliva specimen by the F1 antibody coated to the ELISA plate.

HRP is covalently attached to the F1 antibody using amino and thiol directed cross-linkers per procedures outlined in Ishikawa, E., et.al., 1983, "Enzyme-labeling of antibodies and their fragments for enzyme immunoassay and immunohistochemical staining", J. Immunoassay 4: 209–327.

SALIVA F1 ELISA TEST PROCEDURE:

This procedure describes how to test a saliva specimen for the concentration of F1 antigen contained in the saliva:

1.) Place 100 μl of saliva collected from a person in the well of the F1 ELISA plate;

2.) Cover well with a plate sealer and incubate at room temperature for 3 hours;

3.) Aspirate saliva from well, wash well 3 times with wash buffer and aspirate the buffer washing solution from the well;

4.) Place 100 μl of HRP labeled antibody solution in the well, cover the well with a plate sealer and incubate at room temperature for 2 hours;

5.) Aspirate HRP labeled antibody solution from the well, wash well 3 times with wash buffer and aspirate the buffer washing solution from the well;

6.) Add 100 μl of TMB Substrate (Neogen Corp. K-Blue Substrate cat. #300177) to the well and incubate for 20 minutes;

7.) Add 50 μl of 2N HCL (TMB Stop Reagent) to the well, wait 3 minutes, aspirate the solution from the well;

8.) Use an ELISA plate reader set at 450 nm wavelength to determine the optical density of the material contained at the bottom of the well;

9.) Compare the optical density of the well to a reference curve to determine the concentration of F1 in the saliva specimen.

RESULTS

The following data show the correlation between prothrombin time as expressed by INR or various coagulation conditions and plasma concentrations of the fragments, as well as the correlation between concentrations of the fragments in plasma, saliva, and urine.

For healthy individuals who are not undergoing Warfarin therapy, nor taking pharmaceuticals or vitamins which affect the coagulation system, the concentrations of F1+2, F1, F2, FpA and D-Dimer in blood, urine and saliva are shown in Table A.

TABLE A

AVERAGE CONCENTRATION FOR HEALTHY INDIVIDUALS

|  | BLOOD PLASMA | URINE | SALIVA |
|---|---|---|---|
| F1 + 2 | 0.68 nmol/l | 0.5 nmol/l | 0.14 nmol/l |
| F1 | 0.50 nmol/l | 11.8 nmol/l | 0.10 nmol/l |
| F2 | 0.30 nmol/l | 1.4 nmol/l | 0.06 nmol/l |
| FpA | 1.5 ng/ml | 1.5 ng/ml | 2.47 ng/ml |
| D-Dimer | 77.1 ng/ml | 0.69 ng/ml | 8.35 ng/ml |

When an individual is undergoing anticoagulation therapy with a pharmaceutical such as Warfarin which inhibits the formation of factor Xa, the concentrations of the F1+2, $F_1$, F2, FpA and D-Dimer decrease in the blood and saliva. As their levels decrease the amount of time it takes the blood to coagulate as expressed in INR units increases. Examples of this relationship are shown in Table B for individuals with atrial fibrillation and mechanical heart valves receiving Warfarin anticoagulation therapy for the concentration of F1+2, F1, F2, FpA and D-Dimer in blood. Table C shows the relationship in saliva.

TABLE B

AVERAGE BLOOD PLASMA CONCENTRATION FOR INDIVIDUALS WITH ATRIAL FIBRILLATION AND MECHANICAL HEART VALVES

| INR | F1 + 2 (nmol/l) | F1 (nmol/l) | F2 (nmol/l) | FpA (ng/ml) | D-Dimer (ng/ml) |
|---|---|---|---|---|---|
| 1.0 | 0.76 | 0.57 | 0.35 | 2.28 | 480.00 |
| 1.5 | 0.46 | 0.35 | 0.21 | 1.38 | 285.33 |
| 2.0 | 0.31 | 0.23 | 0.14 | 0.93 | 188.00 |
| 2.5 | 0.22 | 0.17 | 0.10 | 0.66 | 129.60 |
| 3.0 | 0.16 | 0.12 | 0.07 | 0.48 | 90.67 |
| 3.5 | 0.12 | 0.09 | 0.06 | 0.38 | 62.85 |
| 4.0 | 0.09 | 0.07 | 0.04 | 0.27 | 42.00 |

TABLE C

AVERAGE SALIVA CONCENTRATION FOR INDIVIDUALS WITH ATRIAL FIBRILLATION AND MECHANICAL HEART VALVES

| INR | F1 + 2 (nmol/l) | F1 (nmol/l) | F2 (nmol/l) | FpA (ng/ml) | D-Dimer (ng/ml) |
|---|---|---|---|---|---|
| 1.0 | 0.21 | 0.11 | 0.070 | 3.64 | 52.80 |
| 1.5 | 0.09 | 0.07 | 0.042 | 2.21 | 31.38 |
| 2.0 | 0.06 | 0.05 | 0.028 | 1.49 | 20.68 |
| 2.5 | 0.05 | 0.03 | 0.020 | 1.06 | 14.30 |
| 3.0 | 0.03 | 0.02 | 0.014 | 0.77 | 9.97 |
| 3.5 | 0.03 | 0.02 | 0.012 | 0.58 | 6.91 |
| 4.0 | 0.02 | 0.01 | 0.008 | 0.43 | 4.62 |

Generally, the relationship between the concentration of the coagulation marker and INR is expressed by the equation Concentration=$\{-m+b(1/INR)\}$. That is concentration of the coagulation marker is inversely related INR (the higher the INR the lower the concentration).

Disease states associated with an increased risk of thrombus formation have the effect of increasing the levels of F1+2, F1, F2, FpA and D-Dimer in blood, urine and saliva of affected individuals. An example of such individuals having increased levels of F1+2 in their plasma and saliva is shown in Table D.

TABLE D

INDIVIDUALS WITH INCREASED THROMBOTIC RISK

|  | F1 + 2 CONCENTRATION | |
|---|---|---|
| MEDICAL CONDITION | PLASMA (nmol/l) | SALIVA (nmol/l) |
| Myocardial Infarction | 7.6 | 1.6 |
| Venous Thrombosis | 10.0 | 2.1 |
| Sickle Cell Disease | 6.1 | 1.3 |

The concentration of the fragments in saliva being directly correlated to the concentration of the same in plasma, one can infer the coagulation status of an animal or human by using the method of the invention on a saliva sample.

What is claimed is:

1. A non invasive method for determining the blood coagulation status of an animal, characterized by measuring F1+2, F1, F2, FpA, D-dimers, F1+2 combined with F1, or F1+2 combined with F2 in saliva, where the concentrations of F1+2, F1, F2, FpA, D-dimers, F1+2 combined with F1, or F1+2 combined with F2 are inversely correlated to the time it takes blood to coagulate and the probability of bleeding and directly correlated to the probability of in-vivo formation of a thrombus or emboli.

2. A non invasive method for determining the blood coagulation status of an animal, characterized by measuring F1+2, F1, F2, FpA, D-dimers, F1+2 combined with F1, or F1+2 combined with F2 in saliva, where the concentrations of F1+2, F1, F2, FpA, D-dimers, F1+2 combined with F1, or F1+2 combined with F2 are inversely correlated to Prothrombin Time (PT), its expression as INR, and the probability of bleeding, and directly correlated to the probability of in-vivo formation of a thrombus or emboli.

3. The method of claim 1 or 2, wherein the coagulation status is related to a blood coagulation disease or disorder, including acute thrombotic situations such as acute myocardial infarction or pulmonary embolism.

4. The method of claim 1 or 2, wherein the coagulation status is related to the intake of anticoagulant or procoagulant drugs affecting the formation of activated blood Factor X (Factor Xa).

5. The method of claim 1 or 2, wherein the coagulation status is related to a deficiency in vitamin K, protein C or protein S levels, or to an abnormality of protein C or protein S.

6. The method of claim 1 or 2, wherein the means for measuring F1+2, F1, F2, FpA, D-dimers, F1+2 combined with F1, or F1+2 combined with F2 is an immunoassay.

7. The method of any of claims 1 or 2, in a non invasive device for in-vitro analysis of the concentration of a coagulation marker in saliva.

8. The method of claim 7, wherein the concentrations are measured in individuals undergoing Warfarin therapy, and other anticoagulant or procoagulant therapy.

9. The method of claim 1 or 2, wherein the animal is a human.

10. The method of claim 3, wherein the blood coagulation disease or disorder is an acute thrombotic situation.

11. The method of claim 10, wherein the acute thrombotic situation is acute myocardial infarcation.

12. The method of claim 10, wherein the acute thrombotic situation is pulmonary embolism.

13. The method of claim 3, in a non invasive device for in-vitro analysis of the concentration of a coagulation marker in saliva.

14. The method of claim 4, in a non invasive device for in-vitro analysis of the concentration of a coagulation marker in saliva.

15. The method of claim 5, in a non invasive device for in-vitro analysis of the concentration of a coagulation marker in saliva.

16. The method of claim 6, in a non invasive device for in-vitro analysis of the concentration of a coagulation marker in saliva.

* * * * *

UNITED STATES PATENT AND TRADEMARK OFFICE
CERTIFICATE OF CORRECTION

PATENT NO.      : 6,503,724 B1
DATED           : January 7, 2003
INVENTOR(S)     : de Nora et al.

It is certified that error appears in the above-identified patent and that said Letters Patent is hereby corrected as shown below:

Title page,
Item [12], change "De Nora et al." to be -- de Nora et al. --
Item [75], change "Matteo De Nora" to be -- Matteo de Nora --

Drawings,
Fig. 4, change "FIBRIN POLYMER STRAN" to be -- FIBRIN POLYMER STRAND --

Column 3,
Line 14, change "a - complex" to be -- a complex --

Column 4,
Line 32, change "know" to be -- known --

Column 5,
Line 38, change "dinic" to be -- clinic --

Column 7,
Line 18, change "Altemately" to be -- Alternately --
Line 38, change "followed the a" to be -- followed a --

Column 8,
Line 44, change "saliva were" to be -- saliva collection were --

Signed and Sealed this

Eighth Day of April, 2003

JAMES E. ROGAN
*Director of the United States Patent and Trademark Office*